United States Patent [19]
Harrison et al.

[11] Patent Number: 5,968,000
[45] Date of Patent: Oct. 19, 1999

[54] MEDICAL DRESSING

[75] Inventors: Jacqueline Harrison, Kingston Upon Hull; Graham Anthony Smith, Beverley, both of United Kingdom

[73] Assignee: Smith & Nephew Plc, London, United Kingdom

[21] Appl. No.: 08/682,594

[22] PCT Filed: Jan. 27, 1995

[86] PCT No.: PCT/GB95/00164

§ 371 Date: Dec. 5, 1996

§ 102(e) Date: Dec. 5, 1996

[87] PCT Pub. No.: WO95/20415

PCT Pub. Date: Aug. 3, 1995

[30] Foreign Application Priority Data

Jan. 28, 1994 [GB] United Kingdom .................. 9401683

[51] Int. Cl.[6] ...................................................... A61F 13/00
[52] U.S. Cl. ................................. 602/41; 602/56; 604/180
[58] Field of Search ................................ 604/174–180; 602/41–59

[56] References Cited

U.S. PATENT DOCUMENTS 5,380,294  1/1995  Persson .................................... 604/180

FOREIGN PATENT DOCUMENTS 284219  9/1988  European Pat. Off. .

*Primary Examiner*—Richard J. Apley
*Assistant Examiner*—Kim M. Lee
*Attorney, Agent, or Firm*—Larson & Taylor

[57] ABSTRACT

There is described a cannula or catheter dressing comprising a body portion of flexible adherent sheet material for covering a wound site caused by the insertion of a catheter into a patient; and a handle an edge of which defines an aperture for receiving the catheter or cannula wherein the handle comprises a material less flexible than the body portion.

17 Claims, 2 Drawing Sheets

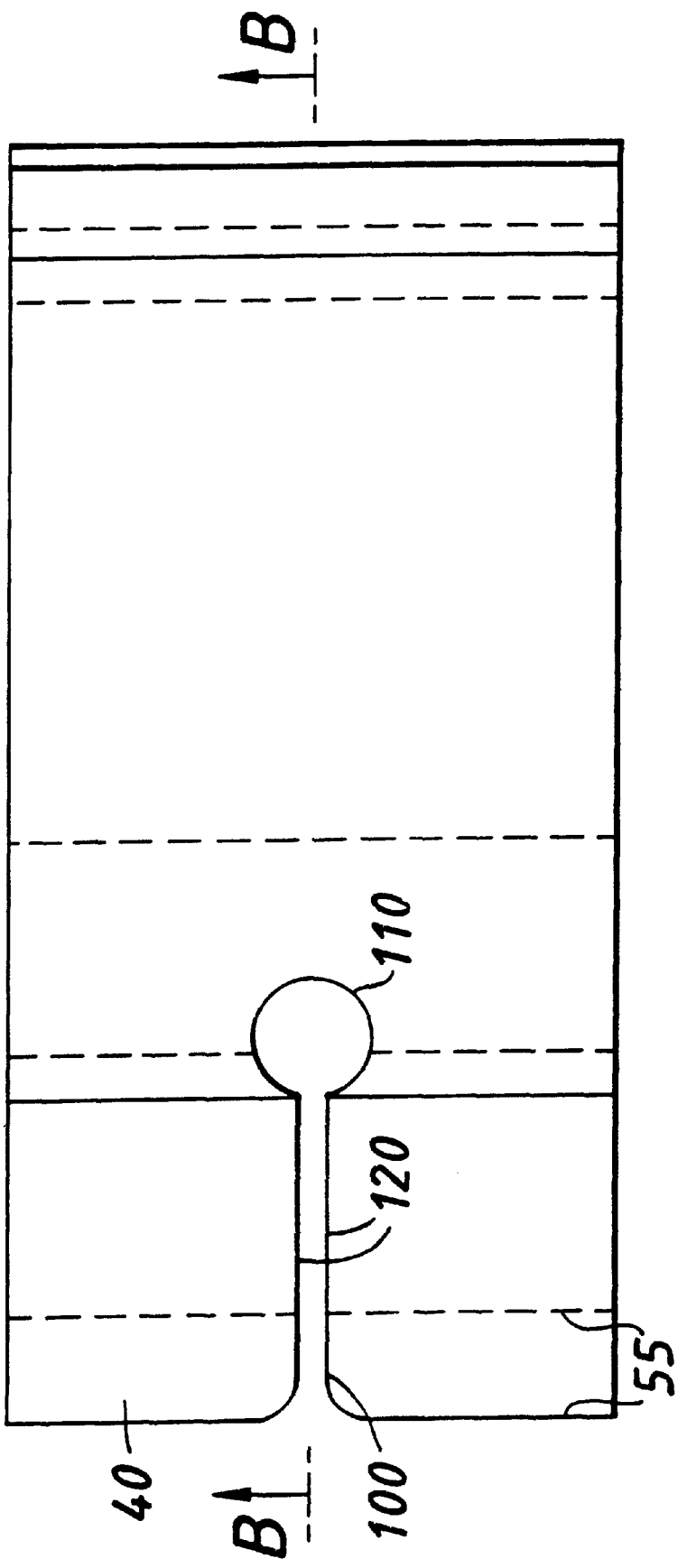

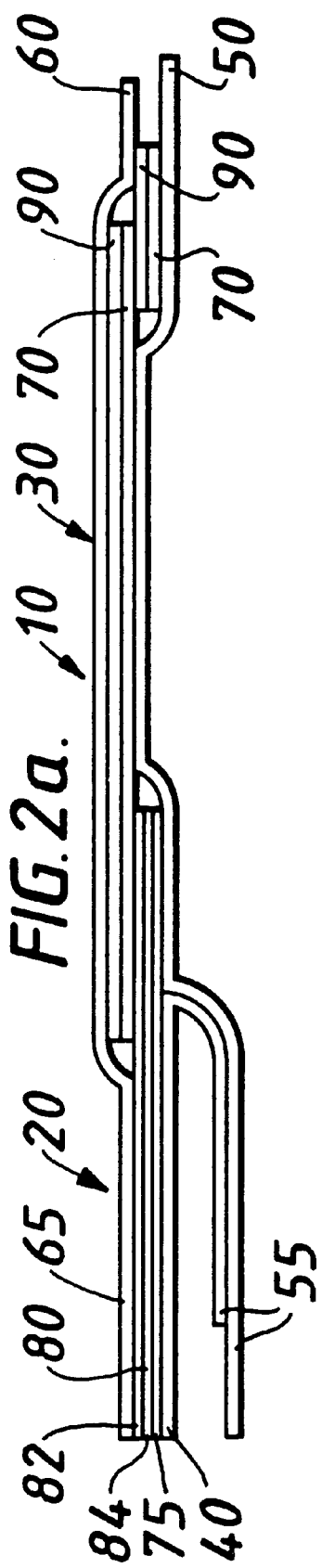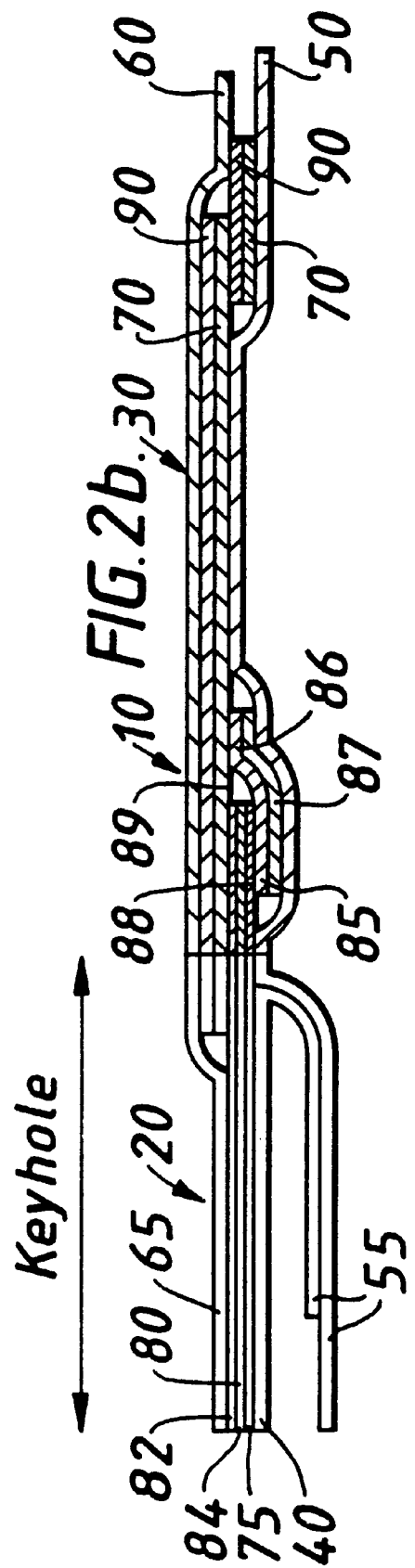

MEDICAL DRESSING

BACKGROUND OF THE INVENTION

1. Field of the Invention

The present invention relates to a dressing for holding a catheter or cannula in place.

2. Description of the Related Art

Commercially available intravenous dressings typically comprise a thin moisture vapour permeable sheet material which has on one surface a skin compatible pressure sensitive adhesive which is in turn covered by a single sheet removable protector. In use the dressing is adhered so as to cover the intravenous access site and the catheter or cannula. One problem with such dressings is that usually a bulky connector or hub is present at the proximal end of the catheter or cannula whereby connection can be made with a source of infusion fluid. This is usually in the form of a female luer lock component. Other devices may be present at this hub such as taps or injection ports or the like. The connector or hub is necessarily exposed to the atmosphere and therefore can provide a pathway whereby bacteria may reach the injection site since the connector cannot be totally enclosed beneath the dressing.

One way of overcoming this problem is to use two types of dressing one covering the injection site and one ensuring that bacteria cannot migrate from the connector along the catheter or cannula to the injection site. This type of dressing is disclosed in European Patent Application No.EP-A-0284219 and includes a handle having an edge which defines an aperture for receiving a connector and a backing film for covering a wound site. The handle is formed of a different material from the backing film and consists of a moisture vapour permeable material coated with adhesive on its body facing side.

Although this arrangement is advantageous in many respects over other prior art cannula or catheter dressings, nursing staff often find this type of dressing difficult to apply.

German Patent No.DE4117282 describes a cannula or catheter dressing which comprises, inter alia, a dressing material provided with a cannula receiving longitudinal slot and one or more handles which lie along an edge parallel to the longitudinal axis of the slot. However, such dressings suffer from the disadvantage that they require the use of two hands to be applied and thus nursing staff generally find them difficult to apply.

Some prior art dressings also suffer from the disadvantage that the junction between a handle portion and a body portion tends to be relatively weak and is often a site of failure of the dressing by the handle separating from the body portion.

We have now found a novel cannula or catheter dressing which overcomes or mitigates the aforementioned disadvantages.

It is a particular disadvantage of prior art dressing which comprise non-integral handles than the juncture between the handle and the body portion is frangible.

SUMMARY OF THE INVENTION

Thus according to the present invention, there is provided a cannula or catheter dressing comprising a body portion of flexible adherent sheet material for covering a wound site caused by the insertion of a catheter or cannula into a patient; and a handle an edge of which defines an aperture for receiving the catheter or cannula wherein the handle comprises a material less flexible than the body portion.

The flexible adherent sheet material preferably comprises an adhesive coated thin film material.

The handle may comprise any material which is less flexible, i.e. is more rigid, than the body portion of the dressing. The increase in the rigidity of the handle portion may be a function of the nature of the material, the thickness of the material or the number of layers of the material.

In particular we provide a cannula or catheter dressing as hereinbefore described wherein the handle comprises a trilaminate material. In a preferred embodiment the handle comprises a wound facing layer of adhesive, a non-wound facing layer of material which is liquid impermeable and moisture vapour permeable, and an intermediate layer of a liquid uptaking material. By the term trilaminate we mean particularly materials comprising three layers, but can include materials which comprise more than three layers, eg. four or five layers.

The dressing of the present invention wherein the handle comprises a handle with a liquid uptaking intermediate is particularly advantageous in that the liquid uptaking material layer can rapidly take up liquid from the surface of the skin (eg. sweat or wound exudate) and hold it away from the skin before it evaporates through the non-wound facing layer of the handle. This is especially advantageous where liquid is released from the skin at a rate higher than that at which it can be evaporated through the upper layer since the liquid uptaking material can act as a temporary reservoir.

A further advantage of the dressing of the present invention is that liquid taken up from the skin surface can enter the liquid uptaking material and spread quickly through this material. This enables liquid evaporating through the non-wound facing layer to evaporate from a much greater surface area than would be the case if the liquid uptaking material were not present and evaporation occurred merely from the skin surface.

The present invention therefore reduces the risk of skin maceration as well as that of fluid building up under the dressing handle and causing the dressing and/or the handle to lift up at its edges. It therefore reduces the risk of bacterial infection and provides increased patient comfort.

The handle may be an integral part of the body portion of the dressing. For example, the whole of the dressing may comprise a single thin film layer an edge of which is bonded, eg. adhesively or laminated, to a second overlying material to produce a handle more rigid than the body portion. In an alternative, the handle may comprise a separate body, eg. a film layer and optionally a trilaminate as hereinbefore described, which is attached to the body portion of the dressing.

When the handle comprises a trilaminate material the non-wound facing layer and intermediate layer may be joined to one another by any appropriate means, eg. by heat lamination, by adhesives, by stitching etc.

The handle can be substantially stronger than prior art handles, which often consist only of thin adhesive coated films. This is particularly the case for trilaminate handles as hereinbefore described in which the intermediate and non-wound facing layers are laminated together in a continuous and co-extensive manner (eg. by heat sealing or by the use of adhesives). Increased strength can reduce the likelihood of tearing or of excessive stretching of the handle. This advantage can greatly increase the likelihood that a catheter or cannula will stay in place.

Desirably the handle and the body portion are formed separately and have different overall compositions. They may be joined together by any conventional means such as adhesive or heat bonding.

In a particularly preferred embodiment of the invention the handle may be connected to the body portion by the handle overlying an edge of the adhesive layer of the body portion. When the handle comprises a trilaminate as hereinbefore described it is the liquid impermeable moisture vapour permeable layer of the handle which is bonded to the adhesive layer of the body portion.

The weakness of the connection between the handle and the body portion may be further alleviated by the presence of a strengthening strip which overlies an edge of the handle and the proximal edge of the body portion. The strengthening strip may lie intermediate the body portion and the handle but preferably overlies the edge of the adhesive layer of the handle and the proximal adhesive layer of the body portion. The strengthening strip may be non-continuous, eg. situated at ends of the body portion and handle junction. Preferably the strengthening strip is continuous and overlies substantially the whole of the body portion and handle junction.

The strengthening strip preferably comprises a thin film material and preferably a liquid impermeable moisture vapour permeable thin film material. The strengthening strip may be adhered to the adhesive layers of the handle and the body portion or it may be provided with an adhesive layer on the handle/body portion facing surface of the strip. In a yet further preferred embodiment the strengthening strip may itself by provided with an adhesive coating on at least its wound facing surface. Preferably the strengthening strip comprises the same material as the body portion of the dressing.

According to a further invention feature of the invention we provide a cannula or a catheter dressing as hereinbefore described wherein the bond between the handle and the body portion has a tensile strength of greater than 0.29 kg f cm$^{-1}$, preferably from greater than 0.29 to 0.4 kg f cm$^{-1}$, more preferably from greater 0.29 to 0.35 kg f cm$^{-1}$, preferably from 0.31 to 0.35 kg f cm$^{-1}$, eg. about 0.34 kg f cm$^{-1}$. The handle and the body portion desirably both have a lower layer of adhesive which forms a wound facing layer. For ease of manufacture, the adhesive layer may be the same for both the handle and the body portion. However, it is preferable that different adhesives are used for the handle and the body portion. For example a stronger adhesive may be desired for the handle than for the body portion since the handle is required to hold a catheter/cannula in place, eg. the luer lock component whereas the main function of the body portion is to cover a wound site. In addition, when an absorbent or liquid uptake layer is incorporated into the handle the handle adhesive may preferably be one which is not absorbed into the liquid uptake material.

Suitably the adhesive layer on the body portion and the handle may be the same or different thickness, each may be 15 to 65 µm thick, preferably is 20 to 40 µm thick, for example 25, 30 or 35 µm thick. Such adhesive layers will generally have a weight of adhesive per unit area of 10 to 75 gm$^{-2}$, more usually 15 to 65 gm$^{-2}$ and preferably 26 to 40 gm$^{-2}$.

Suitable adhesives include those which are described in British Patent No. 1280631 and European Patent Applications Nos. 51935, 35399. Preferably, the adhesive is a polyvinyl ether adhesive such as polyvinyl ethyl ether adhesive or an acrylate adhesive such as an acrylate ester copolymer adhesive. Examples of the latter include acrylate ester copolymers which contain hydrophilic groups, for example a copolymer of 47 parts by weight butyl acrylate, 47 parts by weight 2-ethylhexyl acrylate and 6 parts by weight acrylic acid. Preferably the adhesive on the body portion is an adhesive described in European Patent Application No. 51935 and the adhesive on the handle is one described in European Patent No. 35399. Similarly, the adhesive on the strengthening strip is preferably one described in European Patent No. 51935. It is especially preferred than the adhesive on the body portion and the adhesive on strengthening strip are the same.

The adhesive may be present as a continuous layer or as a discontinuous layer for example as a pattern spread layer.

The present invention can also be advantageous in preventing bacteria from the external environment entering the puncture site in which a catheter or cannula is inserted since a bacteria proof seal around the catheter or cannula or connector can be more easily achieved than with many prior art dressings.

Suitably the adhesive may contain a medicament such as an antibacterial agent. Aptly, the adhesive may contain from 1 to 10% by weight of the adhesive as medicament.

Appropriate antibacterial agents include chlorhexidine and salts thereof such as chlorhexidine diacetate and chlorhexidine digluconate, iodophors such as polyvinyl pyrrolidone-iodine, silver salts such as silver sulphadiazine and polymeric biguanides for example those antibacterial agents known as Vantocil (Trade Mark), which is polyhexamethylene biguanide hydrochloride.

The body portion desirably comprises a polymeric thin film. The film may comprise any of the flexible polymeric films conventionally used in i.v. dressings. The flexible film is aptly a moisture vapour permeable and bacteria proof film. It is most convenient to employ a transparent or translucent material. Favoured moisture vapour permeable, liquid water impermeable, flexible films will have a moisture vapour transmission rate (MVTR) of at least 300 gm$^{-2}$ 24 hr$^{-1}$, more suitably at least 400 gm$^{-2}$ 24 hr$^{-1}$, preferably at least 500 gm$^{-2}$ 24 hr$^{-1}$, and most preferably at least 700 gm$^{-2}$ 24 hr$^{-1}$, for example up to 10,000 gm$^{-2}$ 24 hr$^{-1}$, preferably up to 5,000 gm$^{-2}$ 24 hr$^{-1}$, eg. up to 3,000 gm$^{-2}$ 24 hr$^{-1}$.

When discussed herein, MVTR determinations are based upon the Payne Permeability Cup Method with the cup in an upright position, the temperature at 37° C. and a relative humidity difference of 100% to 10%.

In this method discs of material under test are clamped over Payne Permeability Cups (flanged metal cups) using sealing rings and screw clamps. The exposed surface area of the test sample may be conveniently 10 cm$^2$. Each cup contains approximately 10 ml of distilled water. After weighing the cups are placed in a fan assisted electric oven maintained at 37±1° C. The relative humidity within the oven is maintained at 10% by placing 1 kg of anhydrous 3–8 mesh calcium chloride on the floor of the oven. The cups are removed after 24 hours, allowed to cool for 20 minutes and re-weighed. The MVTR of the test material is calculated from the weight loss expressed in units of grams of weight per square metre per 24 hours.

Suitable flexible films for use in the invention include those described in British Patent No. 1280631 and in European Patent Applications Nos. 51935, 178740 and 196459. Favoured flexible polymeric films include those formed from a polyether or polyester polyurethanes include those known as ESTANES (Trade Mark), which are available from B F Goodrich Corp. Preferred polyurethanes are available as ESTANES 5701, 5702, 5703, 5714 and 580201. A second particularly favoured flexible film may be formed from an elastomeric polyether polyester. Preferred polyether polyesters include HYTREL 4056 (Trade Mark), available from E I du Pont de Nemours & Co. A third particularly favoured polymeric flexible film may be formed from a polyether polyamide. Preferred polyether polyamides include PEBAX 4011 (Trade Mark).

Suitably the thickness of the flexible films used in the body portion of the dressings may be from 9 to 80 μm, more suitably 15 to 50 μm, and preferably 20 to 45 μm, for example from 25 μm to 35 μm and especially 30 μm. Such thicknesses are also suitable for flexible films when used as part of a trilaminate for the handle. When the handle comprises, eg. a relatively rigid film, the thickness of the film may be greater than 80 μm.

A second favoured form of flexible film may be formed from any moisture vapour permeable transparent hydrophilic polymer. Suitable materials include polyurethanes, polyether, polyesters, polyether polyamides, cellulosics and the like.

The most favoured flexible film of hydrophilic polymer for the body portion of the dressing is formed from a hydrophilic polyurethane. Suitable hydrophilic polyurethanes include those having the composition and prepared by the process described in British Patent No. 2093190B. Favoured hydrophilic polyurethanes are those which contain from 5 to 50% by weight of water when hydrated, more suitably 10 to 40% by weight of water. A preferred film of hydrophilic polyurethane has a water content when hydrated of 20 to 30% w/w for example 25% w/w.

When the handle comprises a trilaminate material the moisture vapour permeable film layer is preferably a polyether polyester as hereinbefore described, eg. a HYTREL. The trilaminate handle desirably comprises as its liquid uptaking material an absorbent layer of a woven or a non-woven fabric. Suitable such fabrics include non-woven polyester fabrics, non-woven viscose fabrics or a non-woven polyester viscose blend fabric. The non-woven materials may be apertured, spun bonded or water jet laced/hydroentangled. Particularly suitable fabrics include SONTARA (Trade Mark) 8000 and SONTARA 8010 from Dupont, JETTEX 4003 FB (Trade Mark) and JETTEX 1005 FAV from ORSA (Italy), and ETS 308 from Smith & Nephew (UK).

The absorbent fabrics described above may be used separately or in combination. The weight per unit area of the absorbent material is desirably between 20 gsm and 80 gsm, more preferably between 40 gsm and 50 gsm.

Desirably the handle material exhibits the same moisture vapour permeability properties as the body portion of the dressing, ie. they both have the moisture vapour permeability rates hereinbefore described. However, when the handle comprises a trilaminate material with a water uptaking intermediate layer the overall moisture vapour permeability of the handle may differ from that of the body portion. In such a case the moisture vapour permeability of the non-wound facing film layer of the handle may be the same or different to that of the body portion.

The aperture in the handle of the dressing may be defined by an indentation, ie. it may be defined by an edge of the handle which extends inwards from the outer periphery of the handle.

In this embodiment it is preferred that the aperture is in the form of an elongate slot such that the handle lies perpendicular to the longitudinal axis of the elongate slot. Preferably the slot is keyhole shaped, having generally straight edges which lead inwardly from the periphery of the dressing towards a region of the slot which has a rounded edge. The rounded edge may be, eg. generally circular or generally oval and may be adapted to fit around a connector for a cannula or catheter. Desirably the straight edges are substantially parallel to one another.

In an alternative embodiment, the aperture is not in the form of an indentation but is defined by an edge formed at an inner region of the dressing, which edge does not extend towards the outer periphery of the dressing, which edge does not extend towards the outer periphery of the dressing. The edge desirably defines as rounded shape, eg. a circular or an oval shape so as to fit around a connector.

The aperture can be formed by punching our or cutting an appropriate shape from a precursor of the desired dressing. Alternatively, a series of perforations may provide points of weakness so that an aperture can be provided by a user of the dressing by pressing out an area of the dressing which is marked out by the perforations.

Desirably the rounded edge defines at least part of a generally circular or generally rounded shape with a width across its widest portion of from 0.2cm to 5cm, more preferably from 0.5cm to 2cm.

Preferably the dressing of the present invention is generally square or generally rectangular. Apt dressings may have dimensions of from 3 to 20cm by from 3 to 20cm, more preferably of from 4 to 8cm by from 5 to 12cm.

Aptly the dressing is provided with one or more release sheets covering the adhesive layers of the dressing by which it is to be attached to a body surface. Preferably the handle defines a keyhole shaped aperture and is provided with two release sheets which cover a substantial part of the adhesive layer on the handle and which are desirably disposed substantially symmetrically about the keyhole shape. Desirably a third release sheet covers the remainder of the adhesive of the dressing. The third release sheet is desirably substantially larger than the first and second release sheets (which are preferably about the same size).

Preferably the release sheets each have an exposed tab to aid in gripping so that the release sheets may easily be removed. The tabs of the first and second release sheets may be folded back on themselves and the tab of third release sheet may extend over these tabs to promote removal of the third release sheet by a user before the first and second release sheets are removed.

The release sheets may be formed of silicone coated release paper.

The dressings as hereinbefore described may be manufactured using conventional methods known per se.

The term "handle" when used herein means the part of a dressing which is used to wrap around a catheter/cannula (eg. around wings thereof) so as to secure it in place in order to prevent damage to a patient's blood vessels which might otherwise occur due to movement of the cannula or catheter. This part of the dressing does not normally overlie a wound site when the dressing is in use and may therefore be formed of different material than that part of the dressing used to overlie a wound site.

The term "liquid uptaking material" when used herein includes materials which absorb liquids, such as sweat or wound exudate into the body of the material concerned; non-absorbent materials, eg. those which are able to take up liquid by a wicking action.

A further component which may be present is a support layer, which may be releasably attached to the dressing so as to cover the body portion and the handle. One such support layer is disclosed in European Patent Application No.EP-A-0360458. It may be formed from, for example, a transparent polymeric film such as a polyethylene film or from a silicone or polyethylene coated paper. The support layer need not be formed of moisture vapour permeable material since its function is to provide temporarily a degree of stiffness to the dressing whilst it is being applied in order to minimise creasing. Thereafter it can be removed and discarded.

The present invention will now be described by way of example only with reference to the accompanying drawings; wherein:

BRIEF DESCRIPTION OF THE DRAWINGS

FIG. 1 is a view of the underside of the dressing;

FIG. 2a is a schematic view of a dressing without a strengthening strip; and

FIG. 2b is a longitudinal cross-section through a dressing along line 2b—2b with a strengthening strip.

DESCRIPTION OF THE PREFERRED EMBODIMENT

Referring now to FIGS. 1 and 2, an apertured cannula/catheter dressing 10 comprises a handle 20 and a body portion 30 for covering a skin puncture site where a cannula or catheter is to be inserted.

The dressing 10 is provided with a support layer 60, formed of polypropylene or polypropylenelpolyethylene or other suitable material, which provides a certain amount of rigidity to the dressing 10 to aid in handling during application of the dressing 10 to patient. The support layer 60 is weakly laminated to the body portion 30 and handle 20 by heat sealing and can be easily manually peeled away from the rest of the dressing 10 by using tab 65. Tab 65 extends beyond the body portion 30 towards the handle,in order that it can be freely gripped.

The body portion 30 comprises a flexible sheet 90 formed of a moisture vapour permeable liquid water impermeable material comprising for example a linear polyether or polyester polyurethane or other hydrophilic polymer film, which has a moisture vapour transmission rate of over 1600 gm$^{-2}$ 24 hr$^{-1}$.

Underneath flexible sheet 90 there is present an adhesive layer 70 formed of a skin compatible adhesive such as a polyvinyl ether or polyacrylate ester adhesive which has a moisture vapour transmission rate of approximately 800 gm$^{-2}$ 24 hr$^{-1}$. The combination of the flexible sheet and adhesive can be obtained from Smith & Nephew pic under the Trade Mark of OPSITE IV 3000.

An adhesive layer 75 is provided on the handle 20.

On the handle 20, however, this adhesive is located under an intermediate layer 80. This intermediate layer 80 is formed of an absorbent non-woven material 84 and a water impermeable moisture vapour permeable film 82 which is obtainable from Smith & Nephew Medical Limited (UK). Intermediate layer 80 is laminated to upper layer 65 by heat sealing.

In FIG. 2b the dressing 10 is also provided with a strengthening strip 85 which comprises a layer of film material 86 and an adhesive layer 87. The strip 85 overlies an edge 88 of the handle 20 and the proximal edge 89 of the body portion 30. The dressing may also be provided with an optional film strip which facilitates removal of the release sheet 50.

Underneath the adhesive there are provided silicone coated release sheets 40, and 50 which together cover the whole of adhesive layers 70 and 75. The release sheets 40, and 50 are provided with tabs 55 to enable them to be easily gripped without disrupting adhesive layer 70 and 75.

The tab 55 of release sheet 50 begins at dotted line 35 of FIG. 1 (which is shown only for illustration as it would not be present on the finished dressing) and extends partially over tabs 55 of release sheets 40 and. This is because it is intended that release sheet 50 be removed initially, that wound covering region 30 then be applied over a catheter/cannula tab leading to a wound site or to a connector for such a tube and then release sheets 40 and be removed so that the handle region 20 can be moulded around a catheter/cannula protruding from the dressing 20 (or around a connection device for such a catheter or cannula.

The composition of the handle allows it to be accurately moulded without substantial creasing or rucking so that a catheter or cannula can be accurately held in place and the dressing can form a bacteria-proof seal between a wound site and the external environment.

As can be seen from FIG. 1, the handle 20 comprises an indented edge 100 which defines a keyhole shape. Edge 100 comprises a rounded region 110 for fitting around a component of a cannula or catheter and two substantially parallel straight regions 120.

Once the rounded region 100 has been positioned as desired around a catheter/cannula component (with the wound covering region 30 of the dressing having been adhered over an entry site for the catheter/cannula), the release sheets 40 and 45 can be easily removed from either side of the aperture and the handle can be moulded so as to provide a seal around the catheter or cannula which is impervious to bacteria.

The invention will now be illustrated by way of Example only.

EXAMPLE 1

Tensile Strength Tests

Prepare five strips of the material being examined as representative of the material as possible, each 200 mm in length and of known widths not greater than 25 mm (or cut longitudinally to give strips of that width), so that both surfaces are freely accessible to the regulated atmosphere for 24 hours preceding the test. Determine the breaking load of each strip in turn on a suitable tensilometer having a movable grip with a constant rate of traverse of 270 to 330 mm per minute and a capacity such that when the sample breaks the reading obtained is 15 to 85% of the full-scale deflection. Place one end of the strip in the fixed grip and the other in the movable grip in such a way that the distance between the grips is 100 mm. Repeat the procedure on the other four strips and calculate the average value. Exclude any strip that slips during the test or that breaks within 10 mm of the grips and replace it by another strip.

The results of the test are shown in Table I:

TABLE I

| Sample No. | UNITS | 1 | 2 | 3 | 4 | 5 | MEAN |
|---|---|---|---|---|---|---|---|
| | | 1-Hand Ported Dressing | | | | | |
| Tensile Strength (T) | kg f cm$^{-1}$ | 0.27 | 0.32 | 0.30 | 0.31 | 0.26 | 0.29 |
| | | 1-Hand Ported Dressing with Additional 10 mm HPU Strip | | | | | |
| Tensile Strength (T) | kg f cm$^{-1}$ | 0.39 | 0.33 | 0.31 | 0.32 | 0.33 | 0.34 |

EXAMPLE 2

Method of Manufacture

An adhesive coated RELKOTE 1020 paper was transfer coated onto a SONTARA 8010 non-woven laminated with HYTREL G3548 to form a handle. An elongate slit was made in the handle.

An adhesive coated hydrophilic polyurethane film with MVTR of greater than 3000 gm$^{-2}$ 24 hr$^{-1}$ was laminated to the handle and a strengthening strip applied by lamination and a protector layer applied. A keyhole port was cut out from the slit and discarded and the dressing packed and sterilised.

We claim:

1. A cannula or catheter dressing comprising a body portion of flexible adherent sheet material for covering a wound site caused by the insertion of a catheter or cannula into a patient; and a handle, an edge of which defines an aperture for receiving the catheter or cannula wherein the handle comprises a wound-facing layer of adhesive, a non-wound-facing layer of material which is liquid impermeable and moisture vapor permeable, an intermediate layer of a liquid uptaking material, and is less flexible than the body portion and wherein the intermediate and non-wound facing layers are co-extensive.

2. A cannula or catheter dressing according to claim 1 wherein the handle and body portion are joined together by adhesive bonding.

3. A cannula or catheter dressing according to claim 1 wherein the handle is connected to the body portion by an adhesive coated film strip which overlies an edge of the handle and the proximal edge of the body portion.

4. A cannula or catheter dressing according to claim 1 wherein the bond between the handle and the body portion has a tensile strength of at least greater than 0.29 kg f cm$^{-1}$.

5. A cannula or catheter dressing according to claim 1 wherein the handle partially overlaps the body portion.

6. A cannula or catheter dressing according to claim 1 wherein the body portion comprises a liquid impermeable moisture vapour permeable material.

7. A cannula or catheter dressing according to claim 6 wherein the body portion material has a moisture vapour transmission rate (MVTR) of at least 300 gm$^{-2}$24 h$^{-1}$ when measured at 37° C. and a relative humidity difference of 100% to 10%.

8. A cannula or catheter dressing according to claim 6 wherein the body portion comprises a hydrophilic polyurethane film.

9. A cannula or catheter dressing according to claim 1 wherein different adhesives are used for the handle and the body portion.

10. A cannula or catheter dressing according to claim 1 wherein the thickness of the body portion is from 9 to 80 μm.

11. A cannula or catheter dressing according to claim 1 wherein the thickness of the handle is from 9 to 80 μm.

12. A cannula or catheter dressing according to claim 1 wherein the intermediate layer of the handle comprises an absorbent material.

13. A cannula or catheter dressing according to claim 12 wherein the intermediate layer of the handle comprises SONTARA.

14. A cannula or catheter dressing according to claim 1 wherein the non-wound facing layer of the handle has a moisture vapour transmission rate of at least 300 gm$^{-2}$ 24 h$^{-1}$ when measured at 37° C. and a relative humidity difference of 100% to 10%.

15. A cannula or catheter dressing according to claim 1 wherein the aperture is in the form of an elongate slot.

16. A cannula or catheter dressing according to claim 15 wherein the elongate slot is keyhole shaped.

17. A method of treating a wound caused by insertion of a catheter or cannula which comprises applying a cannula or catheter dressing according to claim 1 to a cannula or catheter site of a patient.

* * * * *